ated arms, each having a proximal end portion providing a
United States Patent [19]
Burgin

[11] Patent Number: 4,502,485
[45] Date of Patent: Mar. 5, 1985

[54] PLASTIC FORCEPS
[76] Inventor: Kermit H. Burgin, P.O. Box 334, Whitestown, Ind. 46075
[21] Appl. No.: 958,795
[22] Filed: Nov. 8, 1978

Related U.S. Application Data
[63] Continuation-in-part of Ser. No. 811,550, Jun. 30, 1977, Pat. No. 4,165,746.

[51] Int. Cl.³ .............................................. A61B 17/28
[52] U.S. Cl. .................................... 128/321; 128/18; 81/302
[58] Field of Search .................................. 128/17–20, 128/321–324, 325, 346; 81/302, 314, 300, 416, 418, 43; 32/62; 433/159, 160

[56] References Cited
U.S. PATENT DOCUMENTS

| 776,302 | 11/1904 | Crockett | 128/17 |
| 1,094,575 | 4/1914 | Joutras | 128/18 |
| 3,835,861 | 9/1974 | Kees et al. | 128/346 |

OTHER PUBLICATIONS
*Surgery, Gynecology and Obstetrics* vol. 68, No. 6 Jan. 1939, pp. 1060–1063.

*Primary Examiner*—Michael H. Thaler
*Attorney, Agent, or Firm*—Barnes & Thornburg

[57] ABSTRACT

A pair of disposable plastic forceps includes elongeated arms, each having a proximal end portion providing a handle and a distal end portion for attachment of a contacting member to each of the arms, and a hinge for movably connecting the arms to one another to provide adjustment of the forceps, the hinge joining the arms intermediate their ends. The hinge selectively rotatably engages the intermediate portion of each arm to hold the arms in selected rotational positions relative to the hinge.

7 Claims, 12 Drawing Figures

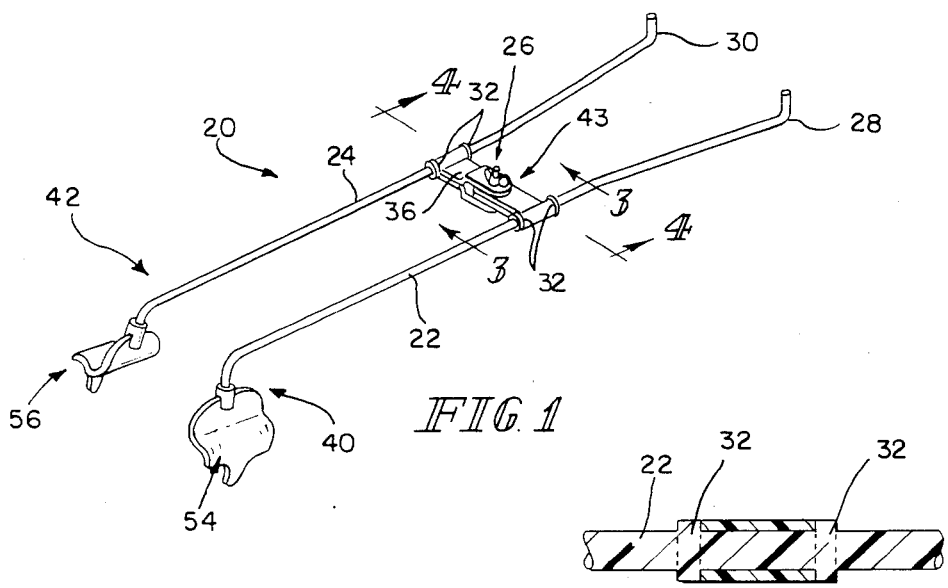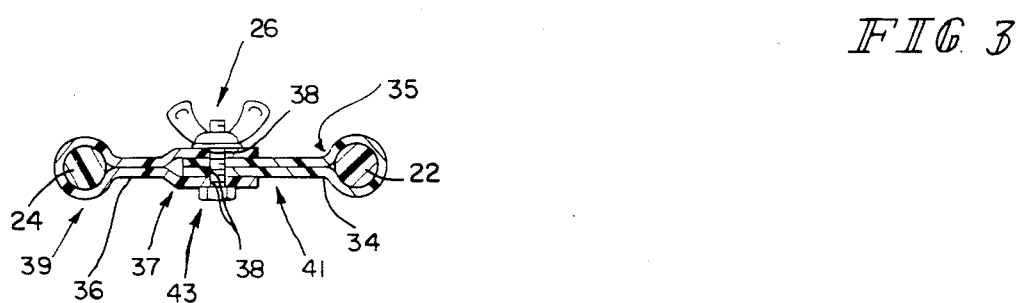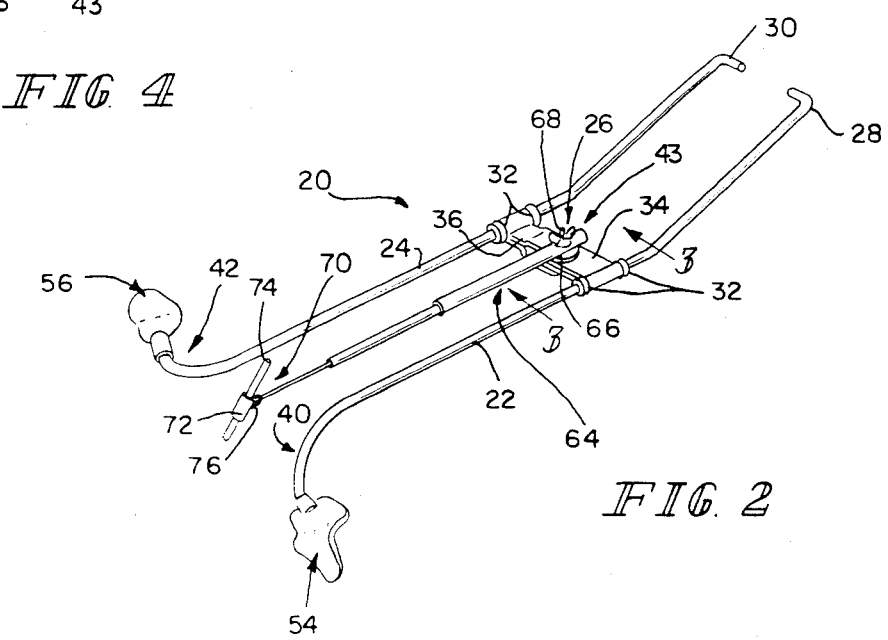

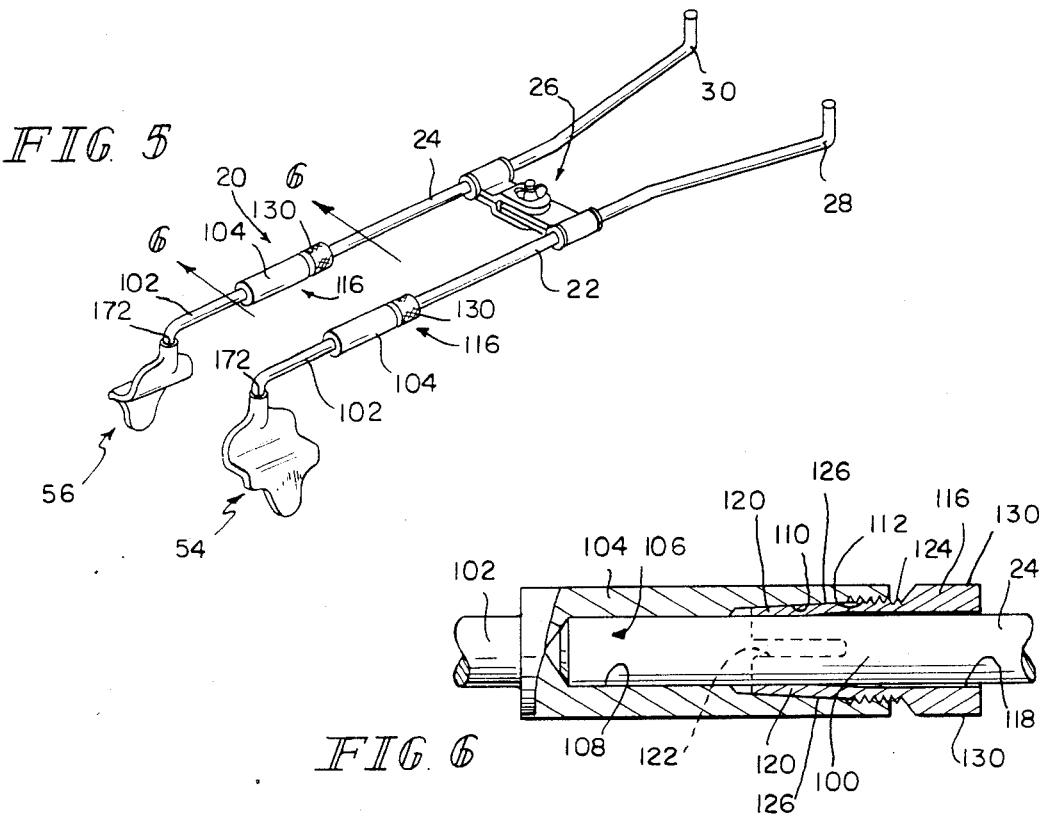

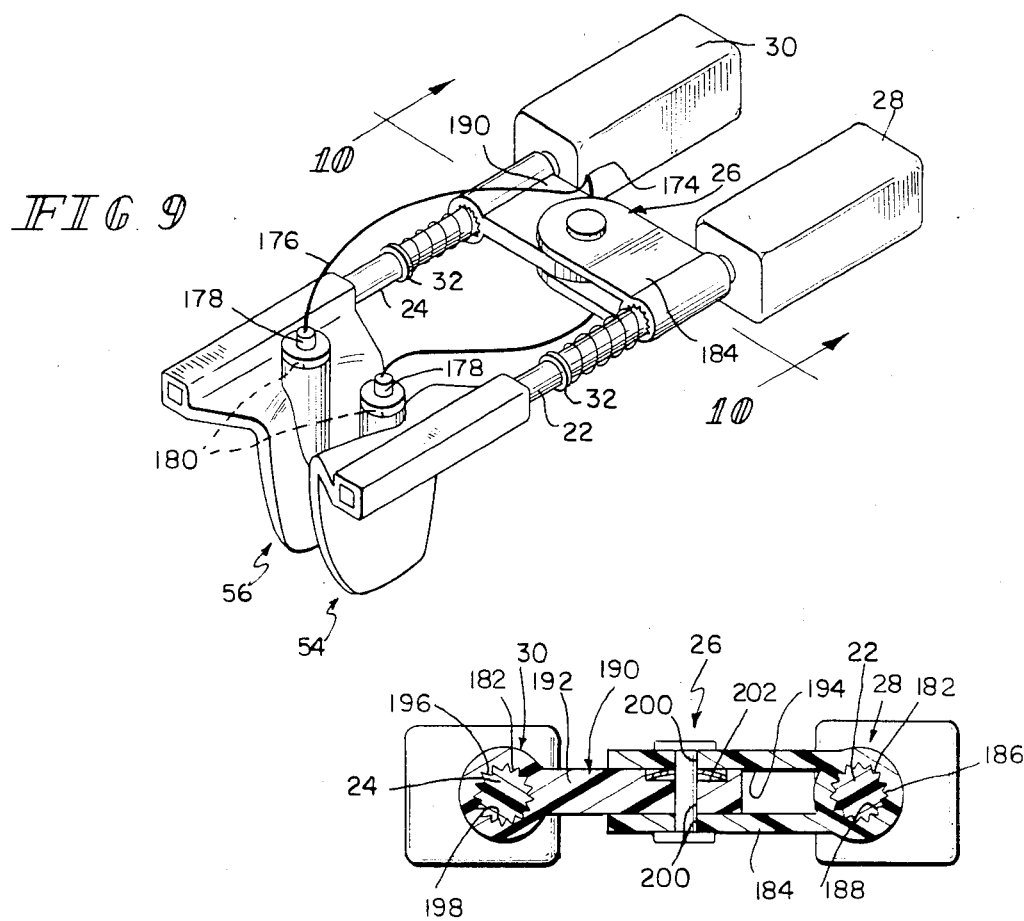
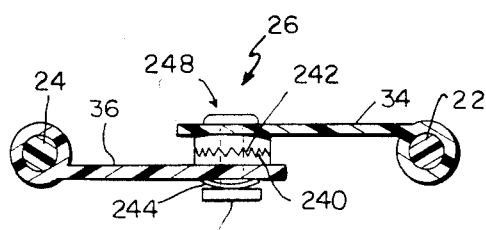
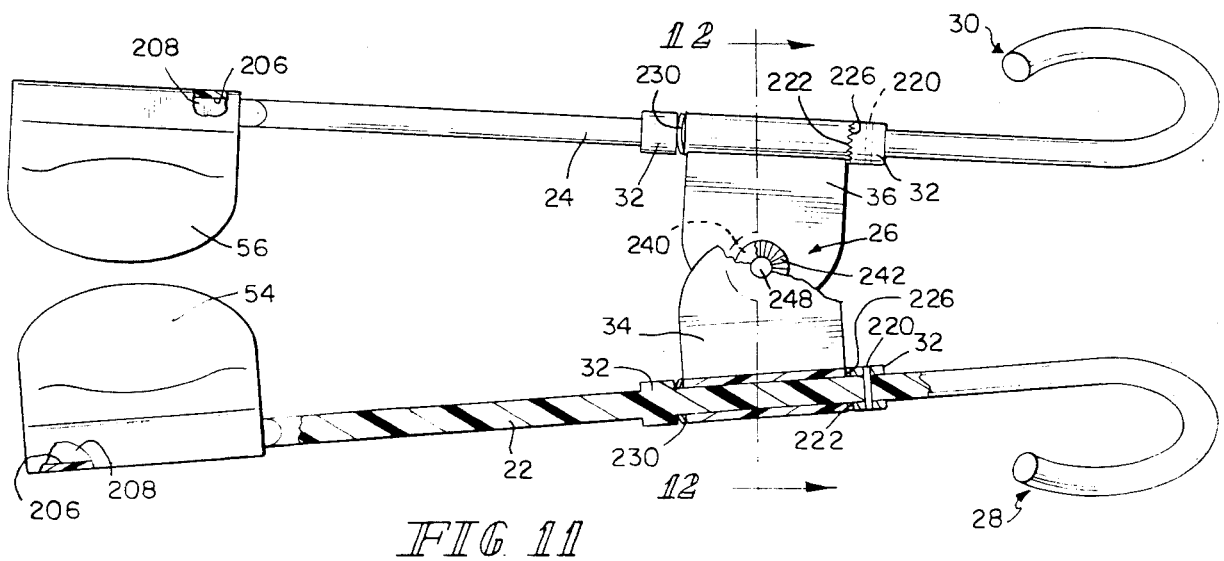

PLASTIC FORCEPS

This is a continuation-in-part of my co-pending U.S. patent application Ser. No. 811,550, filed June 30, 1977, now U.S. Pat. No. 4,165,746.

This invention relates to an apparatus for dilating a meatus or incision, and particularly to disposable plastic forceps having quickly and readily interchangeable contacting members and frictional adjustment means incorporated therein.

There are many well-known specula and forceps for opening or enlarging body orifices or incisions. See for example: Molesworth, U.S. Pat. No. 400,589; Crockett, U.S. Pat. No. 776,302; Joutras, U.S. Pat. No. 1,094,575; Pomerene, U.S. Pat. No. 1,170,324; Radcliff, U.S. Pat. No. 2,217,968; Batista, U.S. Pat. No. 3,853,120; Marco, U.S. Pat. No. 2,544,932; Moore et al, U.S. Pat. No. 3,716,047; and Moore et al, U.S. Pat. No. 3,890.961. Other structures are shown in SURGERY, GYNECOLOGY AND OBSTETRICS, Vol. 68, No. 6, January 1939, pp. 1060-63; Fogerty et al, U.S. Pat. No. 3,503,398; Galiano, U.S. Pat. No. 399,749; Bernardot, French Patent Specification No. 641,915; and Raffaele, Italian Patent Specification No. 246,611.

It is an object of the present invention to provide forceps which are economical to manufacture, such that they can be disposed of after one or several uses, and are divisible into contacting portions which contact the interior of the body upon which the forceps are used, and generally non-contacting portions which do not, and therefore, need not be disposed of. Further, these non-contacting portions can be sterilized by any suitable method.

According to the present invention, there is provided a simple and inexpensive means to attach the contacting portions of the forceps to the non-contacting portion, such that contacting portions are easily and readily interchangeable to accommodate different sizes, shapes and depths of meatuses and incisions. The various sizes and shapes of contacting members are so constructed that they can be inexpensively manufactured. The contacting members are readily attached to, and removed from, the non-contacting members of the forceps.

According to an illustrated embodiment of the invention, disposable plastic forceps include a pair of elongated arms, each having a proximal end portion providing a handle and a distal end portion for attachment of a contacting member to each of the arms. A hinge movably joins the arms to one another to provide adjustment of the forceps, the hinge joining the arms intermediate their ends. The hinge rotatably and frictionally receives the intermediate portion of each arm to hold the arms in selected positions relative to the hinge.

The invention may best be understood by reference to the following description and accompanying drawings which illustrate the invention. In the drawings:

FIG. 1 is a perspective view of an apparatus constructed according to the present invention;

FIG. 2 is a perspective view of the apparatus of FIG. 1, in an adjusted configuration with an attachment provided in accordance with the present invention;

FIG. 3 is a fragmentary sectional view taken generally along section lines 3—3 of FIGS. 1-2;

FIG. 4 is a fragmentary sectional view of the apparatus of FIGS. 1-2 taken along section lines 4—4 thereof;

FIG. 5 is a perspective view of another appartus constructed according to the present invention;

FIG. 6 is a fragmentary sectional view taken generally along section lines 6—6 of FIG. 5;

FIG. 7 is a perspective view of another apparatus constructed according to the present invention;

FIG. 8 is a fragmentary sectional view of the apparatus of FIG. 7 taken generally along section lines 8—8 thereof;

FIG. 9 is a perspective view of yet another apparatus constructed according to the present invention;

FIG. 10 is a fragmentary sectional view taken generally along section lines 10—10 of FIG. 9;

FIG. 11 is a partly sectioned top plan view of yet another apparatus constructed according to the present invention; and FIG. 12 is a fragmentary sectional view taken generally along section lines 12—12 of FIG. 11.

Referring particularly to FIG. 1, disposable plastic forceps 20 include a pair of elongated arms 22, 24 joined by a hinge 26. Each arm 22, 24 includes a proximal end portion 28, 30, respectively, providing a handle or hand grip for the forceps operator. Portions 28, 30 can be formed in any desired angle with respect to the remainder of arms 22, 24, to facilitate easy adjustment of the forceps.

As best illustrated in FIG. 3, each of arms 22, 24 includes a pair of raised annular stops 32 on the intermediate portion of each of arms 22, 24. Stops 32 are spaced apart a predetermined distance to receive therebetween a plastic or metal strap 34 which is shaped as illustrated at 35 in FIG. 4 to conform to the contour of arm 22. Strap 34, when so shaped, rotatably and frictionally receives the intermediate portion of arm 22. The ends of strap 34 are flattened together as indicated at 37. A strap 36, which is also of metal or plastic, is received between stops 32 of arm 24, and is shaped as illustrated at 39 to the contour of the intermediate portion of arm 24. The ends of strap 36 are spaced apart as shown at 41 a sufficient distance so that the ends 37 or strap 34 will fit fairly tightly between them. The ends of both straps 34, 36 are provided with mating holes 38 to receive a bolt or hinge pin 43, thereby forming hinge 26. The bolt is secured in the hinge 26 by a wing nut 45 which is tightened to provide the desired frictional characteristics of hinge 26. It will be seen with reference to FIG. 2 that arms 22, 24 are thereby frictionally pivotally mounted from hinge 26 so that the arms can be turned to various configurations as needed by the forceps operator.

The distal end portions 40, 42 of arms 22, 24, respectively, are bifurcated to provide sockets or slots 44. Each slot 44 includes a pair of side walls 46, 48 and a bottom wall 50. In the illustrated embodiment, each of side walls 46, 48 is provided with a shallow recess or indentation 52. The forceps further include a pair of contacting members 54, 56, which are attached to arms 22, 24, respectively. Since the forceps 20 are useful in many different applications, it is desirable to have many different sizes and shapes of contacting members.

Returning again to FIG. 2, a telescopic attachment 64 is provided. Attachment 64 includes a proximal end 66 shaped for attachment to hinge 26. The illustrated attachment 64 end 66 is attached to hinge 26 by passage of hinge pin 43 through the hole 68 in proximal end 66. However, other suitable attachment means, such as a clip, can be provided. Attachment 64 includes a distal end 70 with a sleeve 72 for receiving a lamp tube 74. Sleeve 72 is joined to the attachment 64 by a ball joint 76. The telescopic attachment 64 including ball joint 76 provides for orientation of the lamp tube 74 to illuminate any desired region of the meatus or incision which the forceps 20 is being used to dilate.

In the other embodiments of the invention described herein, those elements numbered identically with the elements described in connection with FIGS. 1-4 perform the same or similar function.

Referring now to FIGS. 5-6, the disposable plastic forceps 20 includes a pair of elongated arms 22, 24 joined by hinge 26. As before, each arm 22, 24 includes a proximate end portion 28, 30, respectively, providing the operator's hand grip. As best illustrated in FIG. 6, each arm 22, 24 includes a distal end portion 100 having a circular cross-section. The contacting members 54, 56 of the embodiment of FIGS. 5-6 each have the paddle-like ends characteristic of the contacting members of the preceding embodiment. Further, the contacting members 54, 56 of this embodiment are provided with stems 102 having proximal ends 104. Proximal ends 104 are provided with sockets 106 having generally right circular cylindrical interior sidewall portions 108 and tapering frustoconical interior sidewall portions 110. The outer end of each tapering sidewall portion 110 is provided with internally threaded portion 112. The distal end 100 of each arm 22, 24 fits snugly into the right circular cylindrical sidewall portion 108 of a respective socket 106.

The distal end 100 of each arm 22, 24 is provided with a chuck 116 having a central passageway 118 for rotatably receiving the arm 22, 24, a plurality of chuck jaws 120 peripherally spaced apart around the chuck 116 to define slots or spaces 122 which extend longitudinally of the passageway 118 and an externally threaded portion 124 engaging threads 112. The jaws 120 are provided with tapering outer sidewalls 126 engageable with the tapering inner sidewall portions 110 of sockets 106.

In operation, the contacting members are rotated manually to their desired orientations on the distal ends 100 of arms 22, 24. Then the chucks 116 are rotated to engage and tighten the threads 124 into the threads 112. The engagement of the tapering sidewalls 126, 110 forces the jaws 120 tightly against the distal ends 100 of arms 122, 124 locking the contacting members 54, 56 in their selected orientations. The surfaces 130 of chucks 116 are knurled to assist in making this adjustment.

Pivotal adjustment of the hinge 26 is achieved as in the embodiments of FIGS. 1-4.

In the embodiment of FIGS. 7-8, each of arms 22, 24 is provided with a pair of raised annular stops 32 on its intermediate portion. Stops 32 are spaced apart to receive plastic or metal straps 140, 142, 144, 146. Strap 140 includes an upper encircling portion 150. Strap 142 includes a lowering encircling portion 152. Strap 154 includes an upper encircling portion 154. Strap 146 includes a lower encircling portion 156. Straps 140, 146 are slightly longer than straps 142, 144, and extend into overlapping relationship. The overlapping ends 157, 158, respectively, of straps 140, 146 are provided with mating passageways 159 receiving a bolt or hinge pin 43. Bolt 43 is secured in the hinge 26 by a wing nut 45 and is tightened to provide the desired frictional characteristics of hinge 26.

Straps 140, 142 are provided with mating passageways 160 and straps 144, 146 are provided with mating passageways 162. A bolt 164 extends through passageways 160 and is captured thereon by a wing nut 166. A bolt 168 extends through passageways 162 and is captured by a wing nut 170. Wing nut 166 is tightened on bolt 164 to provide the desired frictional characteristics between the upper and lower encircling portions 150, 152 and arm 22 to hold it in a predetermined orientation with respect to hinge 26. Wing nut 170 is tightened on bolt 168 to provide the desired frictional characteristics between upper and lower encircling portions 154, 156 and arm 24 to hold arm 24 in the desired rotational orientation with respect to hinge 26.

The distal ends of the arms 22, 24 in the embodiment of FIGS. 7-8, and the distal ends of the stems 102 in the embodiment of FIGS. 5-6, fit into sockets 172 provided in the paddle-like contacting members 54, 56. The paddle-like portion of contacting members 54, 56 are thus removable from the arms 22, 24 in the embodiment of FIGS. 7-8, or from the stems 102 in the embodiment of FIGS. 5-6. It should be understood, however, that in the embodiment of FIGS. 5-6, the paddle-like portions of the contacting members 54, 56 and the stems 102 can be molded in one piece, along with the socket 106 to form disposable portions for attachment to the distal ends 100 of arms 122, 124.

In the embodiment of the invention illustrated in FIGS. 9-10, the elongated arm 22, 24 proximal end portions 28, 30 are formed to provide hand grips which can be hollow to house, for example, dry cells (not shown). A passageway 174 can be provided through the wall of one of the portions 28, 30 for insulated electrical conductors 176 which are used to supply power to small lamps 178 housed in sockets 180 of the contacting members 54, 56. In this embodiment, the contacting members 54, 56 are formed from an optical wave-guiding plastic, such as polymethylmethacrylate (LUCITE or PLEXIGLAS). Rays of light from the lamps 178 travel outwardly through the ends and edges of the contacting members 54, 56 to illuminate the meatus or incision being opened.

In the embodiment of FIGS. 9-10, as best illustrated in FIG. 10, each of arms 22, 24 is splined, as indicated at 182. The hinge 26 consists of a hinge member 184 having a central passageway 186 for longitudinally slidably receiving the splined portion 182 of arm 22. Passageway 186 includes cooperating splines 188, such that arm 22 can be moved longitudinally to disengage splines 182 from splines 188 to permit rotation of arm 22 and its contacting member 54. When arm 22 reaches a desired rotational orientation, splines 182 are projected longitudinally back into engagement with splines 188, fixing the rotational position of arm 22 in passageway 186. A second hinge 26 part 190 provides a cooperating member 192 which is movably received within a space 194 provided by the hinge part 184. Hinge part 190 is provided with a passageway 196 into which an intermediate portion of arm 24 is longitudinally slidably engaged. Passageway 196 is provided with splines 198 engageable with the splines 182 on arm 24 to prevent rotation of arm 24 in the passageway 196. Arm 24 is selectively rotatably adjustable in the same manner as arm 22 by disengaging splines 182 from splines 198, turning the handle 30 portion of arm 24 and the contacting member 56, and projecting the spline portion 182 of arm 24 back into engagement with splines 198.

The hinge 26 includes mating passageways 200 in members 184 and 192. A recess 202 is provided in a surface of member 192 adjacent a surface of member 184. A Belville washer is housed in recess 202 to contact both of the opposing surfaces of members 184, 192. A rivet completes the frictional engagement of hinge members 184, 192.

In the embodiment of FIGS. 11–12, the contacting members 54, 56 are provided with rectangular cross-section sockets 206. The distal end of each arm 22, 24 is provided with a rectangular cross-section portion 208 cooperating with the sockets 206 for removably positioning the contacting members 54, 56 on the arms 22, 24.

Each of the arms 22, 24 is provided with a pair of raised annular stops 32 on its intermediate portion. For assembly purposes, the rearward stops 32, adjacent the handles 28, 30, are slidable into their positions and are fixed in position by pins 220 extending through transverse bores in arms 22, 24 and mating bores in the annular stops 32. The rearward stops 32 are provided with forward-facing serrated surfaces 222.

The hinge 26 is constructed from two straps 34, 36 located between the stops 32 of arms 22 and 24, respectively. Each of straps 34, 36 is formed to provide a rearwardly-facing serrated surface 226 which cooperates with the forward-facing serrated surface 222 on its respective stop 32. The cooperating serrated surfaces 222, 226 are preloaded into engagement by Belville washers 230 positioned between the forward extents of straps 34, 36 and their respective forward stops 32. To adjust the forceps, the handles 28, 30 are pulled rearwardly (toward the operator) slightly with respect to hinge 26 to disengage the serrated surfaces 222, 226. Arms 22, 24 are then turned to a desired adjustment. Handles 28, 30 are then released to permit the arms 22, 24 to move forward (away from the operator) with respect to the hinge 26 to re-engage the serrated surfaces 222, 226 and lock the arms 22, 24 non-rotatably in their respective hinge straps 34, 36.

The hinge 26 itself includes mating serrated surfaces 240, 242 provided on straps 34, 36, respectively. The serrated surfaces 240, 242 are normallly held in engagement by a Belville washer 244 which urges upwardly between the head 246 of the hinge pin 248 and the strap 36. To pivot the hinge straps 34, 36 with respect to one another, the straps are urged away from one another to disengage the serrated portions 240, 242 against the urging of the Belville washer. The straps 34, 36 are pivoted to a desired orientation and released. The washer snaps the serrated portions 240, 242 into engagement in the desired orientation.

I claim:

1. Disposable forceps including first and second elongated arms, each having a proximal end portion providing a handle and a distal end portion for supporting a contacting member, and a hinge for movable joining the arms to provide adjustment of the forceps, the hinge joining the arms intermediate their ends and including a first portion providing a passageway for receiving an intermediate portion of the first arm, the first portion and first arm being provided with cooperating means for engagement to prevent rotation of the first arm in the first portion in selected rotational orientations of the first arm with respect to the hinge, the first arm being movable longitudinally with respect to the first passageway portion selectively to disengage the engagement means for rotatable adjustment.

2. The apparatus of claim 1 wherein the hinge further includes means providing a second passageway portion for receiving an intermediate portion of the second arm, the second passageway portion and second arm intermediate portion being provided with cooperating means for engagement to prevent rotation of the second arm in the second passageway portion in selected rotational orientations of the second arm with respect to the hinge, the second arm being movable longitudinally in the second passageway portion selectively to disengage the engagement means for rotatable adjustment.

3. The apparatus of claim 2 wherein at least one arm further includes a stop means and a yieldable urging means cooperating with its respective passageway portion to urge the cooperating means for engagement back into engagement to prevent unwanted rotation of the arm in its respective passageway portion.

4. Disposable forceps including first and second elongated arms, each having a proximal end portion providing a handle and a distal end portion for supporting a contacting member, and a hinge for movably joining the arms to provide adjustment of the forceps, the hinge joining the arms intermediate their ends and including a first portion providing a passageway for receiving an intermediate portion of the first arm, the first portion and first arm being provided with cooperating means for engagement to prevent rotation of the first arm in the first portion in selected rotational orientations of the first arm with respect to the hinge, the first arm being movable longitudinally with respect to the first passageway portion selectively to disengage the engagement means for rotatable adjustment, the engagement means comprising cooperating crown wheel-like portions on the first arm and adjacent the first passageway providing portion, and means for yieldably urging said crown wheel-like portions into engagement.

5. Disposable forceps including first and second elongated arms, each having a proximal end portion providing a handle and a distal end portion for supporting a contacting member, and a hinge for movable joining the arms to provide adjustment of the forceps, the hinge joining the arms intermediate their ends and including a first portion providing a passageway for receiving an intermediate portion of the first arm, the first portion and first arm being provided with cooperating means for engagement to prevent rotation of the first arm in the first portion in selected rotational orientations of the first arm with respect to the hinge, the first arm being movable longitudinally with respect to the first passageway portion selectively to disengage the engagement means for rotatable adjustment, the hinge including means providing a second passageway portion for receiving an intermediate portion of the second arm, the second passageway portion and second arm intermediate portion being provided with cooperating means for engagement to prevent rotation of the second arm in the second passageway portion in selected rotational orientations of the second arm with respect to the hinge, the second arm being movable longitudinally in the second passageway portion selectively to disengage the engagement means for rotatable adjustment, comprising cooperating crown wheel-like portions on a respective arm and passageway providing portion, and means for yieldably urging said crown wheel-like portions into engagement.

6. The apparatus of claim 4 or 5 wherein said yieldable urging means comprises spring means between said arm and passageway providing portion.

7. The apparatus of claim 6 wherein said spring means comprises a spring washer.

* * * * *